(12) United States Patent
Baussant et al.

(10) Patent No.: US 7,125,696 B2
(45) Date of Patent: Oct. 24, 2006

(54) METHOD FOR PREPARING A POLYPEPTIDE SOLUBLE IN AN AQUEOUS SOLVENT IN THE ABSENCE OF DETERGENT

(75) Inventors: Thierry Baussant, Bellegarde (FR); Pascale Jeannin, Saint Julien en Genevois (FR); Yves Delneste, Saint Julien en Genevois (FR); François Lawny, Saint Sixt (FR); Jean-Yves Bonnefoy, Le Sappey (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 10/169,953

(22) PCT Filed: Jan. 4, 2001

(86) PCT No.: PCT/FR01/00023

§ 371 (c)(1),
(2), (4) Date: Jul. 3, 2002

(87) PCT Pub. No.: WO01/49705

PCT Pub. Date: Jul. 12, 2001

(65) Prior Publication Data

US 2003/0044915 A1    Mar. 6, 2003

(30) Foreign Application Priority Data

Jan. 4, 2000    (FR)    ................................. 00 00070

(51) Int. Cl.
*C12N 13/00* (2006.01)
*C12N 1/00* (2006.01)
*C12N 1/22* (2006.01)
*C12N 1/12* (2006.01)
*C12P 1/00* (2006.01)

(52) U.S. Cl. ................ 435/173.9; 424/130.1; 424/178.1; 424/184.1; 424/234.1; 424/259.1; 424/400; 424/418; 435/41; 435/173.9; 435/243; 435/252.1; 435/262; 435/272; 436/174; 436/175; 436/177

(58) Field of Classification Search ............ 435/41, 435/70.1, 71.1, 183, 220, 243, 252.1, 262, 435/320.1, 173.9, 272; 436/2, 8, 93.48, 234.1, 436/259.1, 802, 174, 175, 177; 424/130.1, 424/178.1, 184.1, 234.1, 259.1, 400, 418
See application file for complete search history.

(56) References Cited

U.S. PATENT DOCUMENTS 5,814,455 A    9/1998    Provonost et al.
5,846,751 A    12/1998    Provonost et al.

(Continued)

FOREIGN PATENT DOCUMENTS

EP    896883 A1    2/1999

(Continued)

OTHER PUBLICATIONS

Haeuw et al. 1998. Eur. J. Biochem. vol. 255. pp. 446-454.*

(Continued)

*Primary Examiner*—Lynette R. F. Smith
*Assistant Examiner*—J. Hines
(74) *Attorney, Agent, or Firm*—Hueschen and Sage (57) ABSTRACT

A invention concerns a novel method for preparing a polypeptide soluble in an aqueous solvent in the absence of detergent, and polypeptides obtainable by said method. The invention also concerns the use of said polypeptides, in particular for preparing medicines or vaccines, for fighting against bacterial and viral infections or cancers.

4 Claims, 5 Drawing Sheets tP40    rP40s 97 kDa →

66 kDa →

45 kDa →

31 kDa →

21 kDa →
14 kDa →

U.S. PATENT DOCUMENTS 6,197,929 B1  3/2001  Binz et al.
2002/0045703 A1  4/2002  Bassett et al.

FOREIGN PATENT DOCUMENTS

| EP | 1114844 A1 | 7/2001 |
| WO | WO 96 14415 A | 5/1996 |
| WO | WO 97 28264 A | 8/1997 |
| WO | 00/48628 | 4/2000 |
| WO | 00/50071 | 8/2000 |

OTHER PUBLICATIONS

Haeuw et al. 1998. Eur. J. Biochem, vol. 255, paes 446-454.*

Baldermann et al. 1998. J. Bacterial. vol. 180, pp. 3741-3749. Abstract Only.*

Gromiha et al. 1997. Biophy J. vol. 72, pp. 2094-2102. Abstract Only.*

Schultz GE. 2002. Biochim Biophys Acta. vol. 1565, pp. 308-317. Abstract Only.*

Pearson WR and Lipman DJ, Improved tools for biological sequence comparison. Proc. Natl. Acad. Sci. USA 85:2444-2448 (1998).

Needleman SB and Wunsch CD. A General Method Applicable to the Search for Similarities in the Amino Acid Sequence of Two Proteins J. Mol. Biol. 48:443-453 (1970).

Smith TF and Waterman MS. Comparison of Biosequences Advances In Applied Mathematics 2:482-489 (1981).

Cella M, Sallusto F, Lanzavecchia A. Origin, maturation and antigen presenting function of dendritic cells. Curr. Opin. Immunol. 9:10-6 (1997), abstract only.

Steinman RM, Pack M, Inaba K. Dendritic cells in the T-cell areas of lymphoid organs. Immunol. Rev. 156:25-37 (1997), abstract only International Search Report for corresponding application PCT/EP03/04975.

Baldermann C, et al. The regulated outer membrane protein Omp21 from Comamonas acidovorans is identified as a member of a new family of eight-stranded beta-sheet proteins by its sequence and properties. J Bacterial. 180:3741-9 (1998).

Gromiha MM and Ponnuswamy PK Prediction of transmembrane beta-strands from hydrophobic characteristics of proteins. Int J Pept Protein Res. 42:420-31 (1993).

Wantanabe M, et al. Computer simulations of the OmpF porin from the outer membrane of *Escherichia coli*. Biophys J. 72:2094-102 (1997).

Schulz GE The structure of bacterial outer membrane proteins. Biochim Biophys Acta 1565:308-17 (2002).

Baldermann C, et al. The regulated outer membrane protein Omp21 from Comamonas acidovorans is identified as a memeber of a new family of eight-stranded beta-sheet proteins by its sequence and properties. J Bacterial. 180:3741-9 (1998), abs only.

Gromiha MM and Ponnuswamy PK Prediction of transmembrane beta-strands from hydrophobic characteristics of proteins. Int J Pept Protein Res. 42:420-31 (1993), abs only.

Wantanabe M, et al. Computer simulations of the OmpF porin from the outer membrane of *Escherichia coli*. Biophys J. 72:2094-102 (1997), abs only.

* cited by examiner

SEQUENCE LISTING

```
<160> NUMBER OF SEQ ID NOS: 2

<210> SEQ ID NO 1
<211> LENGTH: 1035
<212> TYPE: DNA
<213> ORGANISM: Klebsiella pneumoniae
<220> FEATURE:
<221> NAME/KEY: CDS
<222> LOCATION: (1)..(1032)
<220> FEATURE:
<223> OTHER INFORMATION: P40

<400> SEQUENCE: 1 atg aaa gca att ttc gta ctg aat gcg gct ccg aaa gat aac acc tgg      48
Met Lys Ala Ile Phe Val Leu Asn Ala Ala Pro Lys Asp Asn Thr Trp
  1               5                  10                  15 tat gca ggt ggt aaa ctg ggt tgg tcc cag tat cac gac acc ggt ttc      96
Tyr Ala Gly Gly Lys Leu Gly Trp Ser Gln Tyr His Asp Thr Gly Phe
             20                  25                  30 tac ggt aac ggt ttc cag aac aac aac ggt ccg acc cgt aac gat cag     144
Tyr Gly Asn Gly Phe Gln Asn Asn Asn Gly Pro Thr Arg Asn Asp Gln
         35                  40                  45 ctt ggt gct ggt gcg ttc ggt ggt tac cag gtt aac ccg tac ctc ggt     192
Leu Gly Ala Gly Ala Phe Gly Gly Tyr Gln Val Asn Pro Tyr Leu Gly
     50                  55                  60
```

```
ttc gaa atg ggt tat gac tgg ctg ggc cgt atg gca tat aaa ggc agc      240
Phe Glu Met Gly Tyr Asp Trp Leu Gly Arg Met Ala Tyr Lys Gly Ser
 65                  70                  75                  80 gtt gac aac ggt gct ttc aaa gct cag ggc gtt cag ctg acc gct aaa      288
Val Asp Asn Gly Ala Phe Lys Ala Gln Gly Val Gln Leu Thr Ala Lys
                 85                  90                  95 ctg ggt tac ccg atc act gac gat ctg gac atc tac acc cgt ctg ggc      336
Leu Gly Tyr Pro Ile Thr Asp Asp Leu Asp Ile Tyr Thr Arg Leu Gly
            100                 105                 110 ggc atg gtt tgg cgc gct gac tcc aaa ggc aac tac gct tct acc ggc      384
Gly Met Val Trp Arg Ala Asp Ser Lys Gly Asn Tyr Ala Ser Thr Gly
        115                 120                 125 gtt tcc cgt agc gaa cac gac act ggc gtt tcc cca gta ttt gct ggc      432
Val Ser Arg Ser Glu His Asp Thr Gly Val Ser Pro Val Phe Ala Gly
    130                 135                 140 ggc gta gag tgg gct gtt act cgt gac atc gct acc cgt ctg gaa tac      480
Gly Val Glu Trp Ala Val Thr Arg Asp Ile Ala Thr Arg Leu Glu Tyr
145                 150                 155                 160 cag tgg gtt aac aac atc ggc gac gcg ggc act gtg ggt acc cgt cct      528
Gln Trp Val Asn Asn Ile Gly Asp Ala Gly Thr Val Gly Thr Arg Pro
                165                 170                 175 gat aac ggc atg ctg agc ctg ggc gtt tcc tac cgc ttc ggt cag gaa      576
Asp Asn Gly Met Leu Ser Leu Gly Val Ser Tyr Arg Phe Gly Gln Glu
            180                 185                 190 gat gct gca ccg gtt gtt gct ccg gct ccg gct ccg gct ccg gaa gtg      624
Asp Ala Ala Pro Val Val Ala Pro Ala Pro Ala Pro Ala Pro Glu Val
        195                 200                 205 gct acc aag cac ttc acc ctg aag tct gac gtt ctg ttc aac ttc aac      672
Ala Thr Lys His Phe Thr Leu Lys Ser Asp Val Leu Phe Asn Phe Asn
    210                 215                 220 aaa gct acc ctg aaa ccg gaa ggt cag cag gct ctg gat cag ctg tac      720
Lys Ala Thr Leu Lys Pro Glu Gly Gln Gln Ala Leu Asp Gln Leu Tyr
225                 230                 235                 240 act cag ctg agc aac atg gat ccg aaa gac ggt tcc gct gtt gtt ctg      768
Thr Gln Leu Ser Asn Met Asp Pro Lys Asp Gly Ser Ala Val Val Leu
                245                 250                 255 ggc tac acc gac cgc atc ggt tcc gaa gct tac aac cag cag ctg tct      816
Gly Tyr Thr Asp Arg Ile Gly Ser Glu Ala Tyr Asn Gln Gln Leu Ser
            260                 265                 270 gag aaa cgt gct cag tcc gtt gtt gac tac ctg gtt gct aaa ggc atc      864
Glu Lys Arg Ala Gln Ser Val Val Asp Tyr Leu Val Ala Lys Gly Ile
        275                 280                 285 ccg gct ggc aaa atc tcc gct cgc ggc atg ggt gaa tcc aac ccg gtt      912
Pro Ala Gly Lys Ile Ser Ala Arg Gly Met Gly Glu Ser Asn Pro Val
    290                 295                 300 act ggc aac acc tgt gac aac gtg aaa gct cgc gct gcc ctg atc gat      960
Thr Gly Asn Thr Cys Asp Asn Val Lys Ala Arg Ala Ala Leu Ile Asp
305                 310                 315                 320 tgc ctg gct ccg gat cgt cgt gta gag atc gaa gtt aaa ggc tac aaa     1008
Cys Leu Ala Pro Asp Arg Arg Val Glu Ile Glu Val Lys Gly Tyr Lys
                325                 330                 335 gaa gtt gta act cag ccg gcg ggt taa                                 1035
Glu Val Val Thr Gln Pro Ala Gly *
            340

<210> SEQ ID NO 2
<211> LENGTH: 344
<212> TYPE: PRT
<213> ORGANISM: Klebsiella pneumoniae
<220> FEATURE:
```

-continued

<223> OTHER INFORMATION: P40

<400> SEQUENCE: 2

```
Met Lys Ala Ile Phe Val Leu Asn Ala Ala Pro Lys Asp Asn Thr Trp
 1               5                  10                  15

Tyr Ala Gly Gly Lys Leu Gly Trp Ser Gln Tyr His Asp Thr Gly Phe
            20                  25                  30

Tyr Gly Asn Gly Phe Gln Asn Asn Gly Pro Thr Arg Asn Asp Gln
        35                  40                  45

Leu Gly Ala Gly Ala Phe Gly Gly Tyr Gln Val Asn Pro Tyr Leu Gly
    50                  55                  60

Phe Glu Met Gly Tyr Asp Trp Leu Gly Arg Met Ala Tyr Lys Gly Ser
65                  70                  75                  80

Val Asp Asn Gly Ala Phe Lys Ala Gln Gly Val Gln Leu Thr Ala Lys
                85                  90                  95

Leu Gly Tyr Pro Ile Thr Asp Asp Leu Asp Ile Tyr Thr Arg Leu Gly
            100                 105                 110

Gly Met Val Trp Arg Ala Asp Ser Lys Gly Asn Tyr Ala Ser Thr Gly
        115                 120                 125

Val Ser Arg Ser Glu His Asp Thr Gly Val Ser Pro Val Phe Ala Gly
130                 135                 140

Gly Val Glu Trp Ala Val Thr Arg Asp Ile Ala Thr Arg Leu Glu Tyr
145                 150                 155                 160

Gln Trp Val Asn Asn Ile Gly Asp Ala Gly Thr Val Gly Thr Arg Pro
                165                 170                 175

Asp Asn Gly Met Leu Ser Leu Gly Val Ser Tyr Arg Phe Gly Gln Glu
            180                 185                 190

Asp Ala Ala Pro Val Val Ala Pro Ala Pro Ala Pro Glu Val
            195                 200                 205

Ala Thr Lys His Phe Thr Leu Lys Ser Asp Val Leu Phe Asn Phe Asn
    210                 215                 220

Lys Ala Thr Leu Lys Pro Glu Gly Gln Gln Ala Leu Asp Gln Leu Tyr
225                 230                 235                 240

Thr Gln Leu Ser Asn Met Asp Pro Lys Asp Gly Ser Ala Val Val Leu
                245                 250                 255

Gly Tyr Thr Asp Arg Ile Gly Ser Glu Ala Tyr Asn Gln Gln Leu Ser
            260                 265                 270

Glu Lys Arg Ala Gln Ser Val Val Asp Tyr Leu Val Ala Lys Gly Ile
        275                 280                 285

Pro Ala Gly Lys Ile Ser Ala Arg Gly Met Gly Glu Ser Asn Pro Val
    290                 295                 300

Thr Gly Asn Thr Cys Asp Asn Val Lys Ala Arg Ala Ala Leu Ile Asp
305                 310                 315                 320

Cys Leu Ala Pro Asp Arg Arg Val Glu Ile Val Lys Gly Tyr Lys
                325                 330                 335

Glu Val Val Thr Gln Pro Ala Gly
            340
```

METHOD FOR PREPARING A POLYPEPTIDE SOLUBLE IN AN AQUEOUS SOLVENT IN THE ABSENCE OF DETERGENT

The present invention relates to a novel method for preparing a polypeptide soluble in aqueous solvent in the absence of detergent, and also to the polypeptides which can be obtained using the method according to the invention. The invention also relates to the use of such polypeptides, in particular for preparing medicinal products or vaccines, intended to combat in particular bacterial or viral infections or cancers.

Methods for preparing proteins, in particular when they are hydrophobic in nature or when they are produced in particular by genetic recombination in the inclusion bodies of transformed cells, usually require the addition of detergent during extraction, purification or renaturing steps, in order to obtain a protein soluble in aqueous solvent.

Mention may be made, for example, of American patents U.S. Pat. Nos. 5,846,751 and 5,814,455, which describe a method for preparing antigens for diagnosis, derived from *Helicobacter pylori*, using a method comprising a step for solubilizing *H. pylori* cells in the presence of detergent, followed by a size exclusion chromatography step (molecular sieving), the fractions of molecular mass less than 300 000 Da which exhibit decreased urease activity being chosen after analysis of all the fractions obtained by SDS-PAGE electrophoresis under reducing conditions, and also European patent application EP 0 334 278, which describes a method for purifying *Mycoplasma pneumoniae* protein which does not comprise a step of solubilization in the presence of a denaturing agent.

Mention may also be made, for example, of the method for preparing the recombinant *Klebsiella pneumoniae* OmpA protein, named rP40, described in international patent applications WO 95/27787 or WO 96/14415 and in French patent applications FR 98/14007 and FR 99/01917. For these methods, the final solution of renatured and purified recombinant protein obtained contained 0.1% of zwittergent in order to ensure the solubility of the protein.

However, when such proteins are intended, in particular, to be injected in vivo, the presence of these detergents is potentially toxic (risks of necrosis, etc.).

Furthermore, such methods for preparing proteins, in particular recombinant proteins, requiring the addition of detergent in order to increase their solubility in aqueous solvent, confer on these proteins a tertiary structure which, depending on the nature of the protein prepared, is not the tertiary structure which makes it possible to obtain the best activity for this protein, as demonstrated below in the examples.

Thus, there exists today the need for a method for preparing protein which makes it possible to obtain a protein soluble in aqueous solvent, in particular after renaturation, in the absence of detergent, or in the presence of an insignificant amount, and, where appropriate, which has a tertiary structure different from that obtained using a method for preparing protein which requires the final presence of detergent in order to increase the solubility thereof in aqueous solvent, said different tertiary structure making it possible to obtain better activity.

This is precisely the subject of the present invention.

The present invention relates to a method for preparing a purified solution of polypeptide soluble in aqueous solvent in the absence of detergent, from a purified solution of a polypeptide containing a detergent, characterized in that it comprises the following steps:

a) removing said detergent from said purified solution containing a detergent;
b) solubilizing the polypeptide obtained in step a) in a solution containing a denaturing agent;
c) eluting in aqueous medium the polypeptide solubilized in step b), by molecular sieving on a chromatography column.

The term "polypeptide" is also intended to denote a peptide or a protein, these three terms being used indifferently in the present description.

Surprisingly, the inventors have shown that the novel preparation method according to the invention using a chromatography step of molecular sieving in water makes it possible to obtain a renatured protein, in particular a recombinant membrane protein, soluble in water in the absence of any detergent, in particular potentially toxic when injected in vivo.

The polypeptide contained in said purified solution of a polypeptide containing a detergent may be chosen from the polypeptides purified from a biological sample containing said polypeptide, in particular from cultures of microorganisms or of cells which may or may not be transformed, or from a solution obtained during peptide synthesis.

Among the polypeptides purified from cultures of microorganisms or of cells which may or may not be transformed, preference is given, in particular, to those, purified in the presence of detergent, which have derived from the membrane, in particular the Omp proteins located in the outer membrane of bacteria (Omp for outer membrane protein), such as natural P40 (Omp type A) of *Klebsiella pneumoniae*.

When said polypeptide is a polypeptide produced by chemical synthesis, preference is given to the polypeptides exhibiting strong homology with the outer membrane proteins of Gram-negative bacteria, in particular the polypeptides the sequence of which forms β-sheets which are hydrophobic in nature.

The method according to the invention is preferably characterized in that said purified polypeptide contained in said purified solution of a polypeptide containing a detergent is a hydrophobic polypeptide (or polypeptide which is hydrophobic in nature).

The term "hydrophobic polypeptide (or polypeptide which is hydrophobic in nature)" is intended to denote a polypeptide the sequence of which comprises one or more hydrophobic domains. Such hydrophobic domains may, for example, be determined using the algorithm of Kyte and Doolittle (J. Mol. Biol., 157, 105–132, 1982).

The term "hydrophobic protein" is preferably intended to denote here a polypeptide of which the native or recombinant form or form obtained after chemical synthesis, or else renatured form, is not soluble in aqueous solvent (such as water or in saline solution), or is not soluble in aqueous solvent in an amount sufficient to be used in particular in pharmaceutical compositions, in the absence of detergent.

More preferably, the term "hydrophobic protein" is intended to denote here a polypeptide soluble in aqueous solvent in the presence of detergent or of denaturing agent, such as urea or guanidine hydrochloride, said hydrophobic protein being insoluble or insufficiently soluble in aqueous solvent in the absence of detergent.

The term "renatured" is intended to denote a polypeptide having biological properties similar to the native polypeptide, i.e. it may be decreased, equal or amplified, but, other than these considerations of scale, the consequences of adding one polypeptide or another to a biological sample are similar. Thus, it will be understood that the tertiary structures of the renatured polypeptide according to the definition and of the native polypeptide may be different.

In a preferred embodiment, the invention comprises a method according to the invention, characterized in that said purified polypeptide contained in said purified solution of a polypeptide containing a detergent is a recombinant polypeptide.

In a preferred embodiment, said recombinant polypeptide is chosen from the recombinant polypeptides the native form of which is hydrophobic in nature, which are insoluble in aqueous solvent, or for which the intention is to increase the solubility in aqueous solvent, and/or from the recombinant polypeptides produced in cytoplasmic inclusion bodies of the transformed host cell.

In a preferred embodiment, the invention comprises a method according to the invention, characterized in that said purified polypeptide contained in said purified solution of a polypeptide containing a detergent is a polypeptide the tertiary structure of which is of the β-sheet type, this being a tertiary structure corresponding in particular to the form of the native protein and/or to the form of the recombinant protein, where appropriate after renaturation.

In an embodiment also preferred, said recombinant polypeptide is chosen from the recombinant polypeptides the tertiary structure of the native form of which is of the β-sheet type.

Step a) for removing the detergent, of the method according to the present invention, may be carried out by precipitation, in particular by addition of organic alcohol, but also by dialysis or by gel filtration in organic alcohol.

Step b) for solubilizing the polypeptide obtained in step a) of the method according to the present invention may be carried out by taking up the precipitate, in particular with a denaturing agent, but also by dialysis or by gel filtration in these denaturing agents, such as urea or guanidine hydrochloride.

The invention preferably comprises a method according to the invention, characterized in that step a) for removing the detergent from said purified solution is carried out by precipitation of said polypeptide in the presence of an organic alcohol, preferably ethanol.

The invention preferably also comprises a method according to the invention, characterized in that the denaturing agent used in step b) is urea or guanidine hydrochloride.

In an equally preferred embodiment, the invention comprises a method according to the invention, characterized in that the amino acid sequence of said recombinant polypeptide consists of the complete or partial sequence of an outer membrane protein of bacteria, preferably of Gram-negative bacteria.

The expression "complete or partial sequence" is intended to mean the complete sequence or part of the sequence which makes it possible to obtain the same biological activity or a biological activity similar to that obtained with the polypeptide encoded by the complete sequence. Thus, it may be possible to imagine a polypeptide sequence in which the signal sequence has been deleted, or a polypeptide sequence consisting of various sequences, placed side by side, which may or may not have biological activity and which are not arranged concomitantly in the native protein.

In an even more preferred embodiment, the invention comprises a method according to the invention, characterized in that said polypeptide is the *Klebsiella pneumoniae* OmpA protein of sequence SEQ ID No. 2 or a protein the sequence of which has a percentage identity of at least 80%, 85%, 90%, 95% or 99%, after optimal alignment, with the sequence SEQ ID No. 2.

For the purposes of the present invention, the term "percentage identity" between two amino acid sequences is intended to denote a percentage of amino acid residues identical between the two sequences to be compared, obtained after the best alignment, this percentage being purely statistical and the differences between the two sequences being distributed randomly and over their entire length. The best alignment or optimal alignment is that for which the percentage identity between the two sequences to be compared, determined as below, is highest. Sequence comparisons between two amino acid sequences are conventionally carried out by comparing these sequences after having aligned them optimally, said comparison being carried out by segment or by "window of comparison" so as to identify and compare local regions of sequence similarity. Optimal alignment of the sequences for the comparison may be produced, besides manually, using the local homology algorithm of Smith and Waterman (1981) [Ad. App. Math. 2:482], using the local homology algorithm of Neddleman and Wunsch (1970) [J. Mol. Biol. 48:443], using the similarity search method of Pearson and Lipman (1988) [Proc. Natl. Acad. Sci. USA 85:2444], using computer programs which use these algorithms (GAP, BESTFIT, FASTA and TFASTA in the Wisconsin Genetics Software Package, Genetics Computer Group, 575 Science Dr., Madison, Wis. or BLASTP).

The percentage identity between two amino acid sequences is determined by comparing these two optimally aligned sequences, the amino acid sequence to be compared possibly comprising additions or deletions related to the reference sequence so as to obtain optimal alignment between these two sequences. The percentage identity is calculated by determining the number of identical positions for which the amino acid residue is identical between the two sequences, dividing this number of identical positions by the total number of positions compared and multiplying the result obtained by 100 so as to obtain the percentage identity between these two sequences.

The BLAST program is conventionally used by the inventors and by those skilled in the art to compare and determine the percentage identity between two amino acid sequences. The parameters such as the "gap cost" and the substitution matrix are directly selected by the program as a function of the length of the sequences to be compared. For example, the BLAST program "BLAST 2 sequences" may be used, which is available on the site http://www.ncbi.nlm.nih.gov/gorf/bl2.html, the parameters used being those given by default (in particular for the parameters "open gap penalty": 5 and "extension gap penalty": 2; the matrix chosen being, for example, the "BLOSUM 62" matrix proposed by the program), the percentage identity between the two sequences to be compared being calculated directly by the program.

The invention also comprises a method according to the invention, for modifying the tertiary structure of a hydrophobic recombinant protein, preferably for modifying a tertiary structure of the β-sheet type to a tertiary structure of the α-helix type.

Also surprisingly, the inventors have demonstrated that the recombinant protein obtained according to the preparation method according to the invention conserves the biological properties of the rP40 protein purified as described in international patent application WO 95/27787 or WO 96/14415, and even exhibits certain biological activities which are amplified.

The recombinant P40 protein obtained according to the preparation method according to the invention (named rP40s, "s" for soluble) is in stable form, with α-helices, and is hydrophilic, an unexpected result since the native protein is hydrophobic, and exhibits a β-sheet structure. However, and as will be demonstrated by the examples, the two proteins have similar biological activity, the activity of the protein obtained according to the method according to the invention being even greater than that observed for the native protein, this possibly being due to the fact that the method according to the invention makes it possible to obtain a protein which has a novel tertiary structure which is not generally observed and, in particular, which does not exist naturally. This protein which has such properties is therefore also one of the subjects of the invention.

Thus, the invention comprises the water-soluble polypeptides, characterized in that they are obtained, or can be obtained, using the method according to the invention, especially the recombinant polypeptides, in particular the recombinant polypeptides, where appropriate renatured, and corresponding to a complete or partial sequence of the *Klebsiella pneumoniae* P40 protein of sequence SEQ ID No. 2 or of a protein the sequence of which has a percentage identity of at least 80%, 85%, 90%, 95% or 99% with the sequence SEQ ID No. 2.

The present invention also comprises a polypeptide according to the invention, characterized in that said polypeptide has a tertiary structure of the α-helix type.

The rP40 protein is an OmpA derived from the outer membrane of *Klebsiella pneumoniae*. The extraction and purification of this protein have been previously described in patent applications WO 95/27787 and WO 96/14415.

This protein has properties which are very advantageous from an immunological point of view, in particular for the following activities:
  carrier protein capable of inducing an antibody (AB) response directed against a hapten (polysaccharide or peptide hapten) (cf. patent applications WO 95/27787 and WO 96/14415),
  promotes the development of a cytotoxic response against the antigens with which it is coinjected (cf. patent application FR 99 01917),
  attaches selectively to antigen presenting cells (APCs) such as dendritic cells (DCs) (cf. patent application FR 98 14007).

Thus, this protein is of invaluable advantage in therapeutics in generating a B lymphocyte response (and in particular specific ABs) or a cytotoxic T lymphocyte response against a given molecule, which is introduced into the organism at the same time as rP40 (associated or as a mixture). In addition, by virtue of its ability to attach selectively to APCs, and in particular to dendritic cells, rP40 can be used to promote the targeting, presentation and/or expression of molecules by APCs. Since these cells are responsible for initiating specific B and T lymphocyte responses, rP40 is therefore a considerable tool for generating a specific response by the organism against a given molecule.

The rP40 protein is therefore of value in all pathological conditions in which it proves to be beneficial to induce or amplify a nonexistent or inefficient specific immune response, in particular for one of the following uses:
(i) in therapeutic vaccinology, in particular anticancer or prophylactic vaccinology, particularly anti-infectious vaccinology (viruses, bacteria, parasites, fungi), and
(ii) in chronic or recurrent infections. Its ability to attach to DCs broadens it field of use to diverse pathological conditions in which it is advantageous to target APCs with a chemical or biological molecule. Mention may be made, in particular, of autoimmune diseases, transplant rejection, cardiovascular diseases, inflammatory diseases, infectious diseases or immunodeficiency-related diseases.

DCs play an essential role in the development of an immune response and in the initiation of a specific T lymphocyte response (Steinman R. M. et al., Immuno. Rev. (1997) 156, 25, and Sella M. et al., Curr. Opin. Immunol. (1997) 9, 10). Peripherally, dendritic cells are immature and take up and digest antigens very efficiently. After antigenic stimulation in vivo or stimulation by pro-inflammatory molecules, the DCs which have taken up the antigens migrate into the lymphoid organs. During this migration, the DCs undergo functional and phenotypic modifications which are grouped together under the term maturation. This maturation is characterized by an increase, at their surface, of molecules involved in T lymphocyte activation (such as CD40, CD54, CD58, CD86 and Class I/II MHC), the production of cytokines (such as TNFα and IL-12) and the induction of surface expression of specific molecules (such as CD83 for human cells), and the loss of their ability to process antigen. In the thymus-dependent regions of the lymphoid organs, the DCs which have migrated have acquired powerful immunostimulatory properties and will therefore activate circulating naive T lymphocytes very efficiently.

Thus, molecules which make it possible not only to target DCs but also to induce maturation of these cells are of considerable value in therapeutics in order to induce a specific immune response against a given antigen.

In another aspect, a subject of the invention is thus the use of a polypeptide according to the present invention, alone or as an adjuvant, for preparing a therapeutic composition soluble in water in the absence of detergent.

The invention relates in particular to the use of a recombinant, renatured and water-soluble polypeptide according to the invention, alone or as an adjuvant, for preparing a medicinal product preferably intended to modulate the host's immune response.

The invention also relates to the use of said polypeptide according to the invention, in combination with an antigen or a hapten, for preparing a medicinal product intended to modulate the host's immune response against said antigen or hapten.

The antigen or the hapten may be any compound of therapeutic interest.

Preferably, the hapten is chosen from the group comprising peptides, lipopeptides, polysaccharides, oligosaccharides, nucleic acids, lipids or any chemical molecule capable of inducing an immune response directed specifically against said antigen or hapten.

The antigen or hapten may be used in combination with the polypeptide according to the invention, either in a simple mixture or after coupling to said polypeptide, in particular by chemical bonding, preferably of the covalent bonding type. The covalent bonding may, in particular, be obtained by producing hybrid proteins, the polypeptide thus obtained then being renatured using the method according to the invention.

Thus, preferably, the use of said polypeptide according to the invention is characterized in that the antigen or hapten is coupled to said polypeptide by chemical bonding, preferably the covalent bonding type.

Said polypeptides obtained may be used, according to a method according to the invention in many applications, in particular in human or animal therapeutics, preferably, as already discussed, in any application intended to modulate the immune system and/or response in a mammal.

The invention also comprises the use of said polypeptide according to the invention, for preparing a vaccine, in particular an antiviral, antibacterial or anticancer vaccine.

According to another aspect, the invention comprises a method for modulating the immune system of a mammal against an antigen, in particular a bacterial, viral or tumor antigen, characterized in that it comprises the following steps:
a) isolating immature dendritic cells from a mammal;
b) inducing maturation of said cells isolated in step a) by incubating in the presence of a polypeptide according to the invention;
c) incubating the cells obtained in step b) in the presence of said antigen, or transforming said cells with a vector expressing said antigen;
d) injecting the cells obtained in step c) into a mammal, possibly being the mammal of step a).

In another aspect, the invention comprises a method for modulating the immune system of a mammal, characterized in that it comprises a step of injecting a polypeptide according to the invention, alone or as an adjuvant.

The properties observed for the polypeptides according to the invention, in particular for the rP40s protein, renatured according to a method according to the invention, may be optimized by isolating dendritic cells from a mammal, maturing said dendritic cells ex vivo using a polypeptide according to the invention and then loading them with particular antigens, either externally or after transfection with a plasmid encoding one or more antigen(s) of interest, and reinjecting these antigen-loaded cells into the circulation of said mammal or of another mammal.

This method for modulating the immune system is also one of the subjects of the present invention and may be implemented in particular in the case of cancer, for weakly immunogenic tumors, or for any other chronic or recurrent bacterial, viral, fungal and/or parasitic disease, characterized in particular by a relatively inefficient immune response. Mention may be made, without this list being limiting, of infection with HIV, with respiratory syncytial virus, with the measles or mumps virus, the forms of hepatitis, tuberculosis, mycoses, etc.

In a final aspect, the present invention relates to a therapeutic composition comprising, in a pharmaceutically acceptable medium, at least one polypeptide prepared, or which can be obtained, using a preparation method according to the invention (polypeptide according to the present invention).

The invention also relates to a therapeutic composition, characterized in that it comprises, in a pharmaceutically acceptable medium, at least one adjuvant consisting of a polypeptide according to the invention.

Preferably, the therapeutic composition according to the invention comprises, in a pharmaceutically acceptable medium, at least one polypeptide according to the invention in combination with an antigen or hapten.

The invention also comprises a vaccine, characterized in that it comprises at least one polypeptide according to the invention, free of detergent.

In particular, the vaccine according to the invention comprises at least one adjuvant consisting of a polypeptide according to the invention.

Said vaccine preferably comprises at least one polypeptide according to the invention in combination with an antigen or hapten.

The legends to the figures below, and also the examples which follow, are intended to illustrate the invention without in any way limiting the scope thereof.

LEGENDS TO THE FIGURES

DCs generated from monocytes originating from 2 individuals (□ and ■) were exposed to various concentrations of rP40s. After 4 days, CD83 expression was evaluated by FACS. The results are expressed as percentage of cells expressing CD83.

DCs generated from monocytes originating from 3 individuals (■, □ and) were exposed to various concentrations of rP40s. After 2 days, IL-12 production was evaluated in the supernatants by FACS. The results are expressed in pg/ml.

DCs generated from monocytes originating from 3 individuals (exp. 1, exp. 2 and exp. 3) were exposed to various concentrations of rP40s in the absence (■) or presence (□) of 5 μg/ml of polymyxin B. By way of a control, the DCs from an individual were exposed to 1 ng/ml of lipopolysaccharide (LPS) in the absence (■) or in the presence (□) of 5 μg/ml of polymyxin B. After 2 days, IL-12 production was evaluated in the supernatants by FACS. The results are expressed in ng/ml.

The DCs generated from monocytes originating from one individual were exposed to various concentrations of rP40s (■) and of rP40 (□). After 2 days, IL-12 production was evaluated in the supernatants by FACS. The results are expressed in pg/ml.

Comparison of the anti-TNP antibody levels for the rP40s-TNP conjugates (■) or the rP40-TNP conjugates ( ). TT (□): tetanus toxoid-TNP. FIG. 6A shows the IgG2a responses, expressed as absorbance, for a ½500 dilution of serum. FIG. 6B shows the IgG1 responses expressed in μg of antibody per ml of serum.

FIGS. 7A and 7B represent the percentage lysis obtained (percentage cytotoxicity), calculated using the formula: 100×(lysis from the assay–spontaneous lysis/total lysis–spontaneous lysis), as a function of a range of effector cells (expressed as percentage of effector cells to total cells E/T).

FIGS. 7A and 7B represent the curves thus obtained for EL4 A2/Kb cells loaded (■) or not loaded (●) with the ELA peptide, the HLA A2/Kb mice having been preimmunized in the presence of P40Z (FIG. 7A) or P40S (FIG. 7B).

EXAMPLES

Example 1

Cloning the rP40 Gene into an Expression Vector

The gene encoding rP40 was obtained by PCR amplification using the genomic DNA of *Klebsiella pneumoniae* IP 1145 (Nguyen et al., Gene, 1998). The gene fragment encoding rP40 is inserted into various expression vectors, in particular a vector under the control of the promoter of the Trp operon. The nucleotide sequence and the deduced peptide sequence of rP40 are represented in the sequence listing by the sequences SEQ ID No. 1 and SEQ ID No. 2, respectively. An *E. coli* producer strain K12 was transformed with an expression vector pvaLP40. The rP40 protein is produced in the form of inclusion bodies, with a considerable yield (>10%, g of proteins/g of dry biomass). This example is only an illustration of the expression of rP40, but it can be extended to other bacterial strains and also other expression vectors.

Example 2

Method for Fermenting rP40 Fusion Proteins

An Erlenmeyer flask containing 250 ml of TSM medium (Tryptic Soy Broth, Difco), ampicillin (100 μg/ml, Sigma) and tetracycline (8 μg/ml, Sigma) is innoculated with the recombinant *E. coli* strain described in example 1. After overnight incubation at 37° C., 200 ml of this culture is then used to seed 2 liters of culture medium in a fermenter (Biolafitte, France). Conventionally, the culture medium may be composed of chemical agents supplemented with vitamins and/or yeast extracts. The various supplements used will be optimized by those skilled in the art who wish to induce high bacterial cell growth.

The parameters controlled during fermentation are: pH, agitation, temperature, oxygen level and supply of carbon-based sources (glycerol or glucose). In general, the pH is regulated at 7.0 and the temperature set at 37° C. Growth is controlled by supplying the culture with glycerol (87%) at a constant flow rate (12 ml/h) so as to maintain the dissolved oxygen tension signal at 30%. When the turbidity of the culture (measured at 580 nm) reaches the value of 80 (after culturing for approximately 24 hours), production of the proteins is triggered by adding indole acrylic acid (IAA) at the final concentration of 25 mg/l. Approximately 4 hours after induction, the cells are harvested by centrifugation. Approximately 200 g of amount of wet biomass are obtained.

Example 3

Method for Extracting and Purifying the rP40 Protein

Extraction of rP40

After centifugation of the culture broth (4000 rpm, 10 min, 4° C.), the cells are resuspended in a 25 mM Tris-HCl buffer, pH 8.5. The inclusion bodies are obtained after lysis of the bacteria with lysozyme (0.5 g/liter, 1 hour at ambient temperature/gentle stirring). The inclusion body pellet obtained by centrifugation (15 min at 10 000 g at 4° C.) is taken up in a 25 mM Tris-HCl buffer at pH 8.5 containing 5 mM $MgCl_2$, and then centrifuged (15 min at 10 000 g). The inclusion bodies are solubilized by treatment with a 25 mM Tris-HCl solution, pH 8.5, containing 7 M urea (denaturing agent) and 10 mM of dithiothreitol (reduction of disulfide bridges) for 2 hours at 37° C. Centrifugation for 15 min at 10 000 g makes it possible to remove the insoluble particles.

The suspension is mixed with 13 volumes of 25 mM Tris-HCl buffer, pH 8.5, containing NaCl (8.76 g/l) and Zwittergent 3-14 (0.1%, w:v). The solution is left overnight at ambient temperature with gentle stirring in contact with the air in order to promote renaturation of the proteins by dilution and reoxidation of the disulfide bridges.

Purification of the rP40 Protein

Anion Exchange Chromatography Step

After further centrifugation, the solution is dialyzed against 100 volumes of 25 mM Tris-HCl buffer, pH 8.5, containing 0.1% Zwittergent 3-14 overnight at 4° C.

The dialysate is loaded onto a chromatography column containing a support of the strong anion exchanger type (Macro Prep High Q gel, Biorad) equilibrated in the buffer described above at a linear flow rate of 15 cm/h. The proteins are detected at 280 nm. The rP40 protein is eluted, with a linear flow rate of 60 cm/h, for a concentration of 0.2 M of NaCl in the 25 mM Tris-HCl buffer, pH 8.5; 0.1% Zwittergent 3-14.

Cation Exchange Chromatography Step

The fractions containing the rP40 protein are mixed and then concentrated by ultrafiltration by means of an Amicon cell system with stirring, used with a Diaflo membrane of the YM10 type (10 kDa cutoff threshold), for volumes of the order of 100 ml, or by means of a Millipore Minitan tangential flow filtration system, used with membrane plates having a 10 kDa cutoff threshold, for larger volumes. The fraction concentrated is dialyzed overnight at 4° C. against a 20 mM citrate buffer, pH 3.0, containing 0.1% of Zwittergent 3-14.

The dialysate is loaded onto a column containing a support of the strong cation exchanger type (Biorad Macro Prep High S gel) equilibrated in the 20 mM citrate buffer, pH 3.0, containing 0.1% Zwittergent 3-14. The rP40 protein is eluted (rate 61 cm/h) for a 0.7 M concentration of NaCl. The electrophoretic profiles show a degree of purity of the order of 95%. The state of the protein is monitored by SDS-PAGE.

Example 4

Implementation of the Method According to the Invention. Production of rP40s Protein Removal of Zwittergent 3-14 by Precipitation of rP40 with Ethanol Cold ethanol (−20° C.) is added to the purified solution of rP40 (approximately 4 mg/ml) in a ratio of 5 to 1. After one hour at 4° C., the solution is centrifuged for 10 min at 10 000 g. The precipitate is taken up in a solution of 7 M urea in water, so as to achieve an rP40 concentration of 2 mg/ml.

Renaturation of rP40 in Water by Molecular Sieving

The solution of rP40 in 7M urea is loaded onto a column of Fractogel EMD Biosec (volume loaded: 5% of the column volume). The rP40s is eluted at a linear rate of 30 cm/h. The peak containing the rP40s is collected and the eluate is sterilized by filtration and stored at 4° C.

Depending on its tertiary structure, the rP40 protein has a characteristic electrophoretic (migration) behavior. The hydrophobic native form (β-sheet structure) in fact has an apparent molecular mass which is lower than the form exhibiting an α-helix structure. It is observed that the rP40s protein obtained according to the method according to the invention is in the α-helix form, which is hydrophilic and stable.

Demonstration of the Conformational Modifications Between rP40 and rP40s rP40, the *Klebsiella pneumoniae* OmpA, has the property of changing apparent mass by SDS-PAGE depending on the conformational state of the protein ("heat modifiable protein", see Rosenbusch, J. Biol. Chem. (1974), 249: 8019–8029). Without heating to 100° C. in the presence of the buffer used to take up the sample for SDS-PAGE, the native protein, consisting of β-sheets, has an apparent mass of approximately 32 kDa, whereas the heat-denatured protein has an apparent mass of 38 kDa. The denatured form adsorbs less SDS, which explains this decreased migration in the electrophoresis gel. This decreased adsorption of SDS is due to α-helix structures (Nakamura and Mizushima, J. Biochem, (1976), 80: 1411–1422).

Figure 1:
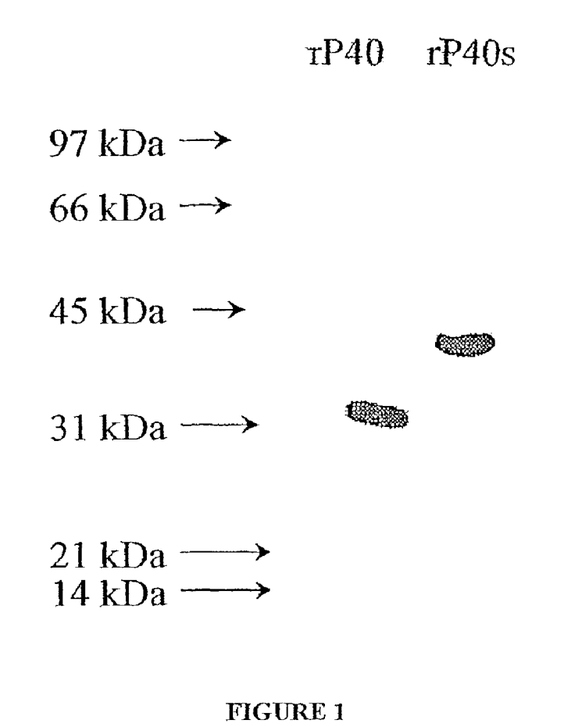
FIG. 1: Comparison of the apparent mass of nonheated rP40 and rP40s on polyacrylamide gel SDS PAGE was carried out on the nonheated proteins. Column 1: molecular mass marker; column 2: rP40; column 3: rP40s.

As shown in FIG. 1, the nonheated rP40, as prepared in example 3, has an apparent mass of 32 kDa (β-sheets), whereas the rP40s, also nonheated, has an apparent mass of 38 kDa, characteristic of α-helix structures.

Example 5

Induction of Maturation of Human Dendritic Cells by rP40s

Example 5 shows that rP40s induces expression of the CD83 molecule and production of IL-12 by human DCs. These two parameters are associated with the process of maturation of human DCs. In particular, expression of the CD83 molecule characterizes mature DCs, this molecule not being expressed on immature DCs.

Induction of Expression of the CD83 Molecule on Human DCs

Isolation of Immature Human Dendritic Cells in vitro

The human dendritic cells are isolated from monocytes isolated from peripheral blood. The blood is sampled by leukapheresis in the presence of an anticoagulant, such as for example lithium heparinate. Mononuclear cells (MNCs) are isolated from healthy individuals by centrifugation on a Ficoll-Hypaque gradient (density=1.077) (Amersham Pharmacia Biotech, Uppsala, Sweden). Briefly, the blood cells are centrifuged at 1500 rpm for 30 minutes at ambient temperature. The MNCs, located at the Ficoll-plasma interface, are recovered and washed twice in the presence of PPMI 1640 medium (Life Technologies, Cergy-Pontoise, France).

The monocytes are purified by positive selection using a magnetic cell separator (MACS™; Miltenyi Biotex, Bergisch Gladbach, Germany) in agreement with the manufacturer's instructions. Briefly, the MNCs are incubated for 20 minutes at 4° C. with magnetic beads to which an anti-human-CD14 monoclonal antibody is attached. After washing, the cell plus beads suspension is loaded onto a column and subjected to a magnetic field. After three washes, the column is no longer subjected to the magnetic field and the monocytes are collected by gravitation. The purity of the monocytes is evaluated by flow cytometry (FACScan flow cytometer; Becton Dickinson, Erembodegem, Belgium) on the basis of the parameters of size-granulosity of the cells. The purity is greater than 98%.

The monocytes are then cultured at a concentration of $5 \times 10^6$ cells/ml in the following medium (subsequently named complete culture medium): RPMI 1640 medium supplemented with 10% of decomplemented (heating at 56° C. for 30 minutes) fetal calf serum, 2 mM of L-glutamine, 50 U/ml of penicillin and 50 μg/ml of streptomycin (Life technologies) in 6-well culture plates (Nunc, Roskilde, Denmark) in a proportion of 5 ml of medium per well. The cells are activated with 20 ng/ml of recombinant human 1IL-4 and 20 ng/ml of recombinant human GM-CSF (R & D Systems, Abingdon, United Kingdom).

After culturing for 6 days (37° C., 5% $CO_2$ in humid atmosphere), the phenotype of the cells is defined by flow cytometry. Briefly, an aliquot of the cell suspension is removed. The cells are washed in FACS buffer (10 mM phosphate buffer, pH 7.4, containing 1% of bovine serum albumin and 0.01% of sodium azide) and then distributed into wells of a cone-bottomed 96-well culture plate (Nunc) in a proportion of $2 \times 10^5$ cells in a volume of 50 μl of FACS buffer. Either a fluorescein-labeled anti-human-CD1a antibody (Becton Dickinson) or a fluorescein-labeled anti-human-CD83 antibody (Becton Dickinson) is added to each well. After incubation for 20 minutes at 4° C., the cells are washed three times with 200 μl of FACS buffer and then resuspended in 200 μl of this same buffer. Analysis of the expression of CD1a versus CD83 is evaluated by FACS. Only the immature dendritic cells characterized by expression of the CD1a molecule (mean fluorescence intensity (MFI)>100) and absence of expression of the CD83 molecule were used.

Flow Cytometry Analysis of CD83 Expression on DCs

The immature DCs were collected, washed and then returned to culture in complete medium at a concentration of $10^5$ cells in a volume of 200 μl in flat-bottomed 96-well culture plates (Costar, Cabridge, USA). The cells are incubated with rP40s. After culturing for four days, expression of the CD83 molecule is evaluated by FACS using an anti-CD83 antibody revealed with a fluorescein-labeled anti-mouse-immunoglobulin antibody (Silenus, Hauworth, Australia). The control isotypic antibodies used originate from Becton Dickinson. The cells are washed in FACS buffer and are then distributed into wells of a conical-bottomed 96-well plate, in the proportion of $2 \times 10^5$ cells in a volume of 50 μl of FACS buffer. An antibody is added to each well. After incubation for 20 minutes at 4° C., the cells are washed three times with 200 μl of FACS buffer and are then resuspended in 200 μl of this same buffer. Analysis of expression of the surface markers is evaluated by FACS.

Figure 2:
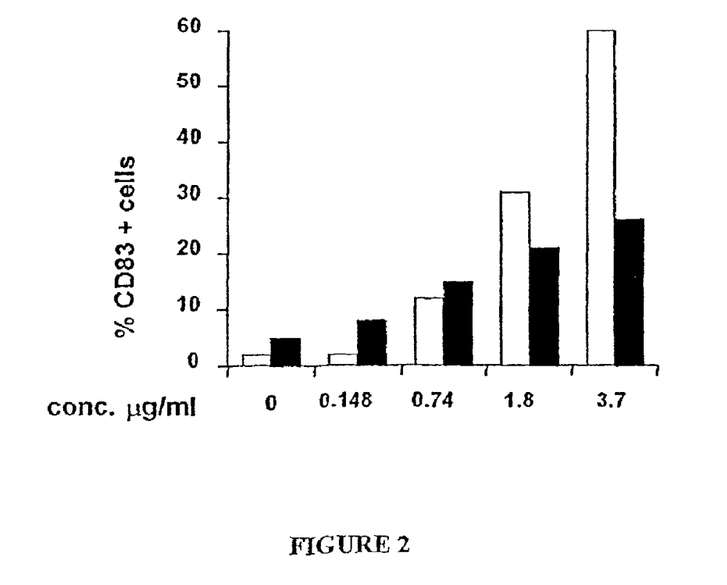
FIG. 2: rP40s induces CD83 expression on human DCs

The results given in FIG. 2 show that rP40s induces, in a dose-dependent manner, expression of the CD83 molecule on a fraction of the immature DCs. Identical results were obtained with the cells originating from two different individuals (■) and (□).

rP40s Induces IL-12 Production by Human DCs

Evaluation of Interleukin 12 (IL-12) Production by DCs

The immature DCs obtained as described in example 4 are collected, washed and then returned to culture in complete medium at a concentration of $10^5$ cells in a volume of 200 μl in flat-bottomed 96-well culture plates (Costar, Cabridge, USA). The cells are incubated with rP40s. After culturing for two days, the concentration of the active IL-12 p40/p35 heterodimer (IL-12 p75) in the supernatants without cells was determined using a flow cytometry immunofluorescence assay (Bioergonomics, St. Paul, Minn.) according to the manufacturer's recommendations (sensitivity of 5 pg/ml).

Figure 3:
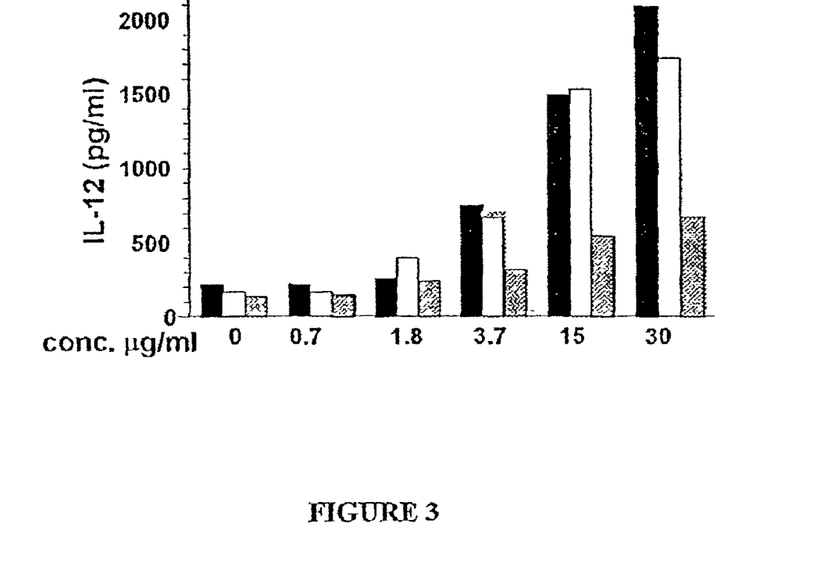
FIG. 3: rP40s induces interleukin (IL)-12 production by human DCs

The results given in FIG. 3 (expressed in pg/ml or in ng/ml) show that rP40s induces production of the biologically active IL-12 dose by human DCs, which depends on the concentration of rP40s. The results were obtained with the cells originating from three different individuals (■, □ and ).

Example 6

The Effect of rP40s on DC Maturation is not due to Contaminating Endotoxins Endotoxins and in particular lipopolysaccharides (LPS) are molecules which induce very rapid and considerable maturation of DCs. The immature DCs were therefore exposed to rP40s in the presence of polymyxin B in order to exclude the fact that the effect of rP40s on DC maturation may be due to contaminating endotoxins. Polymyxin B inhibits the effect of LPS.

Immature DCs obtained from monocytes as described in example 5 were collected, washed and then returned to culture in complete medium at a concentration of $10^5$ cells in a volume of 200 µl in flat-bottomed 96-well culture plates (Costar, Cabridge, USA). The DCs are incubated with rP40s or with lipopolysaccharide (LPS) (purified from the *Escherichia coli* strain isotype 0111: B4; Sigma) in the absence or in the presence of 5 µg/ml of polymyxin B sulfate (Sigma). After culturing for two days, the level of biologically active IL-12 p40/p35 heterodimer (IL-12 p75) in the culture supernatants is measured by ELISA, using a commercial kit (R & D Systems) according to the manufacturer's recommendations (sensitivity of 0.5 pg/ml).

Figure 4:
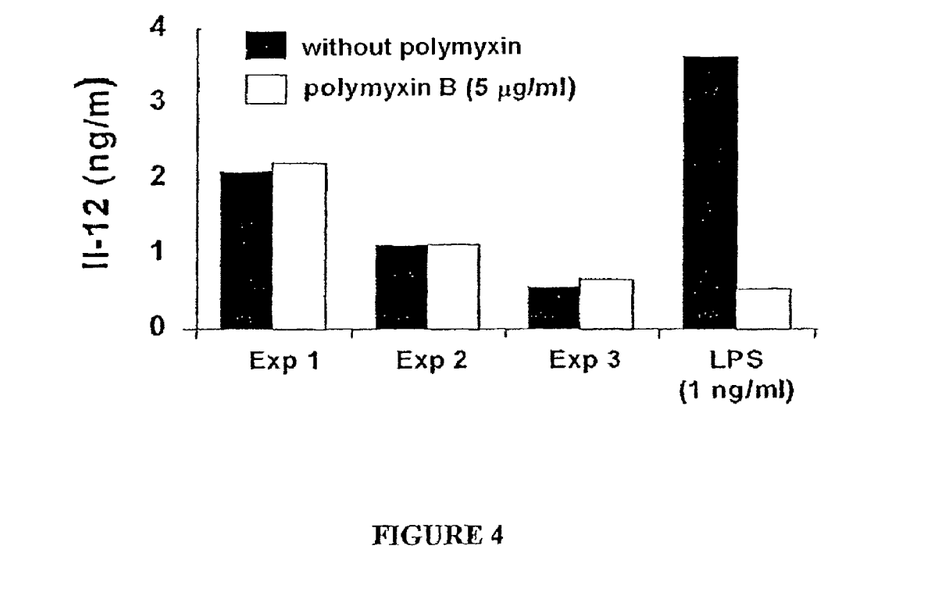
FIG. 4: IL-12 production induced by rP40s is not inhibited by polymyxin B

The results (expressed in ng/ml) show that:

LPS induces IL-12 production by DCs, the effect of LPS on IL-12 production by DCs is inhibited by polymyxin B, the effect of rP40s on IL-12 production by DCs is not inhibited by polymyxin B (the results obtained using the cells derived from 3 different individuals are given in FIG. 4).

In addition, polymyxin B does not inhibit expression of the CD83 molecule on the DCs induced by rP40s (data not shown).

Thus, all these data show that the effect of rP40s on the maturation of human DCs is not due to the presence of contaminating endotoxins, but that clearly the rP40s protein obtained according to the method according to the invention has biological activity which allows dendritic cell maturation.

Example 7

Figure 5:
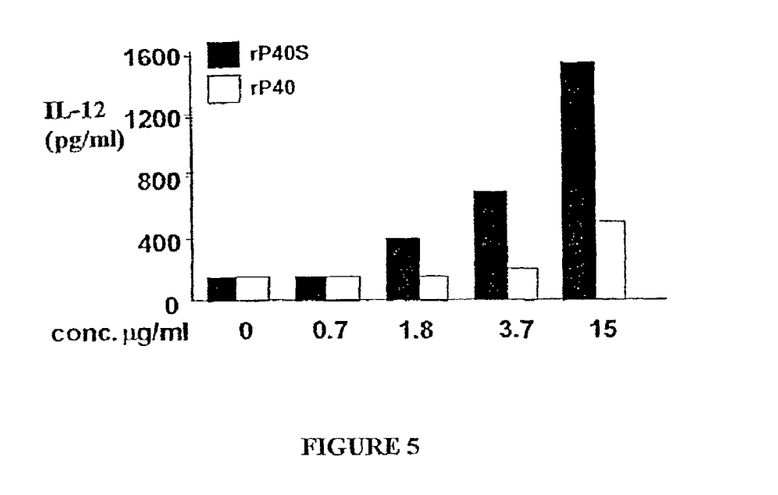
FIG. 5: rP40s induces greater IL-12 production by DCs than rP40

The rP40s Molecule Purified and Renatured According to the Invention Induces much Greater Maturation of DCs than the rP40 Molecule The effect of rP40s and of rP40 on DC maturation was compared. FIG. 5 shows that rP40s induces much greater IL-12 production than rP40.

Immature DCs obtained as described in example 5 were collected, washed and then returned to culture in complete medium at a concentration of $10^5$ cells in a volume of 200 µl in flat-bottomed 96-well culture plates. The DCs are incubated with rP40s or with rP40. After culturing for two days, the bioactive IL-12 was assayed in the supernatants as described in example 5.

The results (expressed in pg/ml) show that rP40s is much more effective than rP40 in inducing IL-12 production by DCs.

It is also possible to show that rP40s is also much more effective than rP40 in inducing CD83 expression on immature DCs (data not shown).

Thus, all these results show that rP40s, purified and renatured according to the method described in the present invention, induces maturation of human DCs and has a biological activity similar to and greater than the rP40 protein purified according to conventional techniques.

Example 8

Induction of Anti-TNP Antibodies by rP40-TNP and rP40s-TNP

Preparation of rP40-TNP, rP40s-TNP and KLH-TNP Conjugates

The solution of TNP-sulfonic acid (Sigma) at a final concentration of 25 mM is added to the solution of protein (1 mg/ml, in 0.1M $Na_2CO_3$). Three proteins are coupled: rP40, rP40s and KLH (Pierce). After incubation for five hours at ambient temperature in the dark, the solution is dialyzed into PBS overnight.

Immunization of Animals and Determination of the Anti-TNP Antibody Response

100 µg of conjugates are injected intraperitoneally into Balb/c mice (n=5), on D0 and D21, in the presence of alum. The serum is taken on D14 and D30. The anti-hapten antibody response (anti-TNP IgG1a and IgG2a) is determined by ELISA using plates coated with TNP-BSA, prepared using the same protocol as above.

Figure 6A:
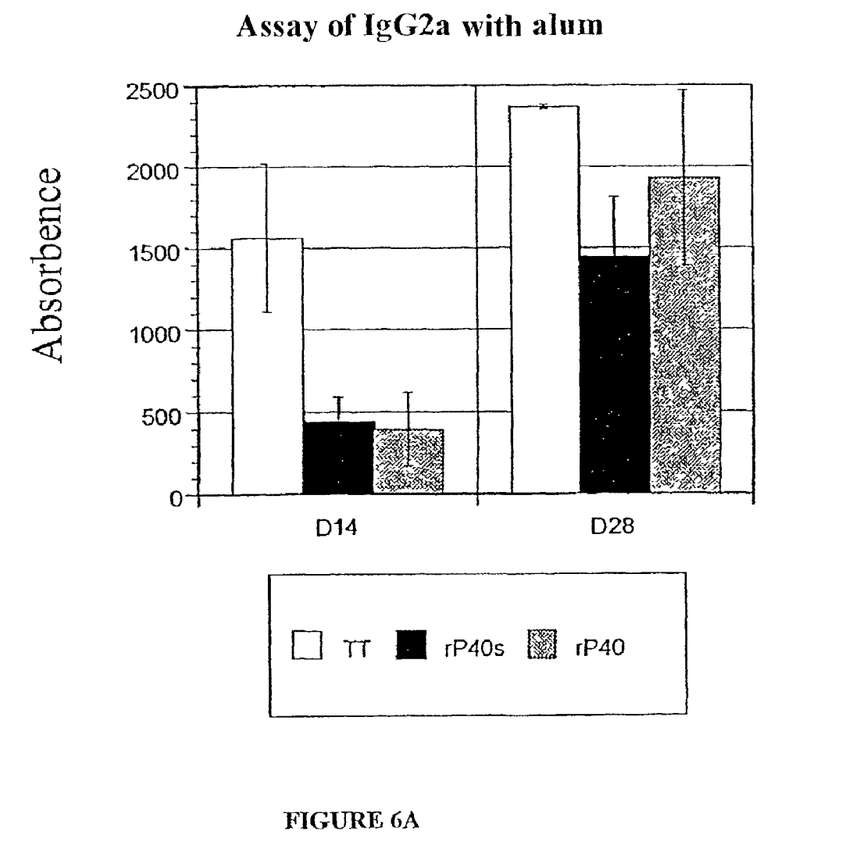
FIGS. 6A and 6B: Induction of an anti-hapten antibody response

The Anti-TNP Antibody Response Induced by the rP40s-TNP Conjugates is Similar to that Induced by the rP40-TNP Conjugates FIG. 6A illustrates the anti-TNP IgG2a antibody responses induced, respectively, by the tetanus toxoid-TNP (TT), rP40s-TNP (rP40s) and rP40-TNP (rP40) conjugates. The anti-TNP antibody responses are expressed as optical density for a 2500-fold serum dilution. As shown in the figure, the responses induced by the rP40s and rP40 conjugates are statistically similar at the two times tested. The response induced by the TT conjugates is earlier.

Figure 6B:
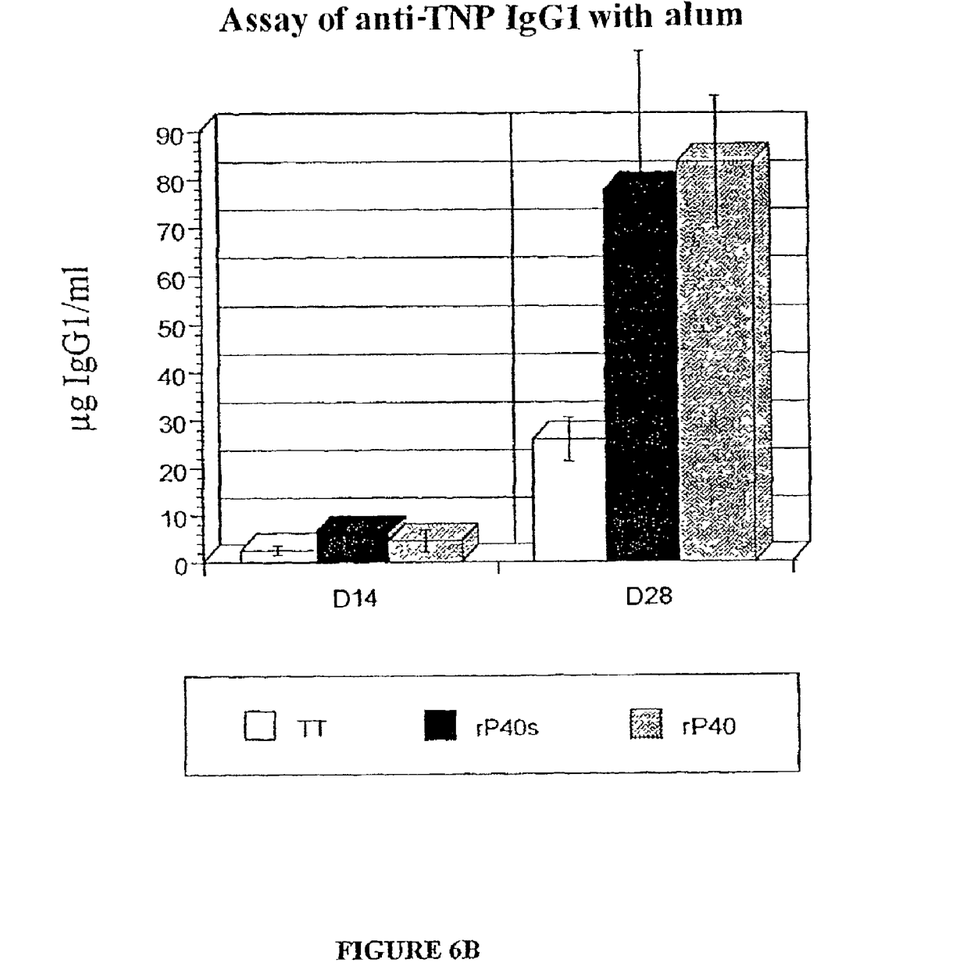

FIG. 6B illustrates the anti-TNP IgG1 antibody responses induced, respectively, by the tetanus toxoid-TNP (TT), rP40s-TNP (rP40s) and rP40-TNP (rP40) conjugates. The antibody responses are expressed in µg of anti-TNP antibody per ml. The figure shows that, for this type of antibody, the responses are also similar for the rP40s and rP40 proteins, these responses being largely greater than those observed for the TT conjugates.

The rP40s protein has the same properties as rP40 in terms of induction of an anti-hapten response.

Example 9

Induction of a Cytotoxic Response by rP40-ovalbumin and rP40s-ovalbumin Conjugates Preparation of rP40-ova and rP40s-ova Conjugates rP40s and rP40 are conjugated to ovalbumin by glutaraldehyde coupling according to the Avrameas method (Avrameas and Terninck, Immunochemistry (1969), 6: 53).

Immunization of Animals and Determination of the CTL Response Induced

100 µg of rP40s-ovalbumin (rP40s-ova) and rP40-ovalbumin (rP40-ova) conjugates in 200 µl of PBS are injected into 5- to 8-week-old female C57BL/6 mice ($H-2^b$). The animals are sacrificed 7 days after immunization and the spleens are removed.

$40 \times 10^6$ spleen cells are cultured in 25 cm² flasks in 10 ml of cDMEM medium, for five days, in the presence of $7 \times 10^6$ irradiated (4000 rad) E.G7 cells.

In the cytolysis assay, the target cells (EL-4, EL-4 pulsed with the SIINFEKL peptide and E.G7) are incubated with 100 μCi/10$^6$ cells of sodium chromate ($^{51}$Cr) for four hours at 37° C. and washed three times with cDMEM medium, before use. The effector cells, consisting of the spleen cells from the restimulation cultures, are cultured with 10 000 $^{51}$Cr-labeled target cells for five hours. After incubation, 100 μl of supernatant from the cultures prepared in triplicate are removed and counted. Table 1 below represents the results obtained, these results being expressed as percentage of specific lysis for three effector cell/target cell ratios: 100:1, 33:1, 11:1.

TABLE 1

| Percentage of specific lysis obtained in the cytolysis assay | | |
|---|---|---|
| | EL4-peptide cells | EL4 cells alone |
| rP40s-ova | 40/20/14 | 5/1/0 |
| rP40-ova | 67/39/20 | 6/6/6 |
| rP40 | 5/5/5 | 5/5/5 |
| ova | 35/27/16 | 36/25/12 |

The results obtained with rP40s are similar to those obtained with rP40; the capacity of the rP40s conjugates to induce a cytotoxic response is of the same order as that of the rP40 conjugates.

Example 10

Comparative Test of Soluble P40 (P40S) Versus Zwittergent P40 (P40Z) for Induction of a CTL Response Directed Against the ELA Peptide For this experiment, 6-week-old HLA A2/Kb mice are injected subcutaneously, at the base of the tail, with a P40Z+ELA or P40S+ELA mixture, at a ratio of 300:50, in the absence of any adjuvant. The carrier/peptide ratio was chosen as a function of data available for the P40Z molecule and may not be the optimal ratio to be used for the P40S mixture.

Ten days after injection, the mice are sacrificed and a cell suspension is prepared from the inguinal and para-aortic lymph nodes which drain the site of injection of the product. The cells are placed in culture and stimulated, in vitro, by adding EL4 A2/Kb cells loaded with the ELA peptide and irradiated. 7 days later, a further stimulation of the effector cells, in vitro, as described above, is carried out and then, after a further 5 days of culturing, a cytotoxicity assay using the $^{51}$Cr method is carried out. In this assay, the EL4 A2/Kb target cells, loaded with the peptide and labeled with $^{51}$Cr, are mixed together with a range of effector cells for 4 hours, and the amount of $^{51}$Cr released is estimated by counting γ radiation. EL4 A2/Kb cells not loaded with the peptide and treated in the same way are used as a control for nonspecific lysis.

For these two types of cell, the percentage cytotoxicity is calculated using the formula:

100×(lysis from the assay−spontaneous lysis/total lysis−spontaneous lysis).

Two curves are plotted: one, from the data obtained with the nonloaded EL4 A2/Kb cells, corresponds to the nonspecific lysis; the other, from the EL4 A2/Lb cells loaded with the peptide. Subtraction of these two curves (represented in FIGS. 7A and 7B) gives the activity of the product.

Figure 7A:
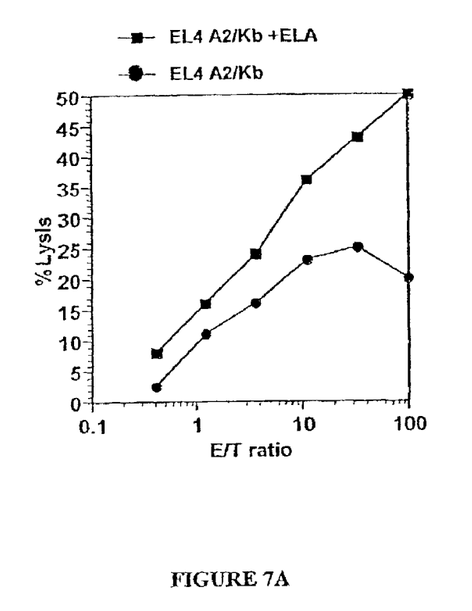
FIGS. 7A and 7B: Comparative test of soluble P40 (P40S, FIG. 7B) versus Zwittergent P40 (P40Z, FIG. 7A) for induction of a CTL response directed against the ELA peptide
Figure 7B:
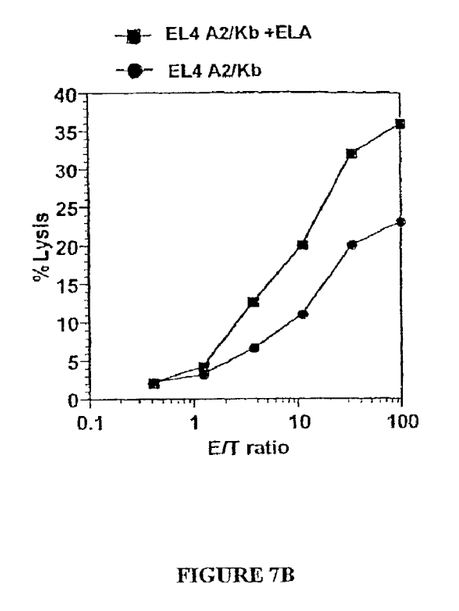

The results given in FIGS. 7A and 7B show that P40S coadministered with ELA (FIG. 7B) is capable of inducing the generation of an anti-peptide cytotoxic response in a manner comparable to P40Z (FIG. 7A)

This result is all the more surprising since, unlike P40Z, for which many tests to set up the P40/peptide ratio were carried out in order to obtain this type of result, no tests to set up P40S were carried out. It is therefore probably possible to notably improve this result.

The invention claimed is:

1. A method for preparing a purified solution of polypeptide soluble in aqueous solvent in the absence of detergent, from a purified solution of a polypeptide containing detergent, said polypeptide being a Klebsiella pneumoniae membrane protein OmpA having the sequence of SEQ ID No. 2 which method comprises the following steps:
   a. removing the detergent from the purified solution containing a detergent;
   b. solubilizing the polypeptide obtained in step a) in a solution containing a denaturing agent selected from the group consisting of urea and guanidine hydrochloride; and
   c. eluting in aqueous medium the polypeptide solubilized in step b), by molecular sieving on a chromatography column;

whereby a tertiary structure of the polypeptide which is a β-sheet type is modified to an α-helix type.

2. The method of claim 1, wherein the purified polypeptide contained in the purified solution of a polypeptide containing a detergent is a hydrophobic polypeptide.

3. The method of claim 1, wherein the purified polypeptide contained in the purified solution of a polypeptide containing a detergent is a recombinant polypeptide.

4. The method of claim 1, wherein step a) for removing the detergent from the purified solution is carried out by precipitation of the polypeptide in the presence of an organic alcohol, preferably ethanol.

* * * * *